United States Patent
Tan et al.

(10) Patent No.: US 10,039,785 B2
(45) Date of Patent: *Aug. 7, 2018

(54) HUCBC TREATMENT OF AMYLOID-ASSOCIATED DISEASE

(71) Applicants: Jun Tan, Tampa, FL (US); Paul R. Sanberg, Spring Hill, FL (US)

(72) Inventors: Jun Tan, Tampa, FL (US); Paul R. Sanberg, Spring Hill, FL (US)

(73) Assignee: University of South Florida, Tampa, FL (US)

(*) Notice: Subject to any disclaimer, the term of this patent is extended or adjusted under 35 U.S.C. 154(b) by 66 days.

This patent is subject to a terminal disclaimer.

(21) Appl. No.: 15/195,243

(22) Filed: Jun. 28, 2016

(65) Prior Publication Data
US 2016/0303165 A1  Oct. 20, 2016

Related U.S. Application Data

(60) Division of application No. 12/706,510, filed on Feb. 16, 2010, now Pat. No. 9,402,870, which is a continuation of application No. PCT/US2008/073265, filed on Aug. 15, 2008.

(60) Provisional application No. 60/956,040, filed on Aug. 15, 2007.

(51) Int. Cl.
A61K 35/12    (2015.01)
A61K 35/16    (2015.01)
A61K 35/44    (2015.01)

(52) U.S. Cl.
CPC .............. A61K 35/16 (2013.01); A61K 35/44 (2013.01); *A61K 2035/122* (2013.01)

(58) Field of Classification Search
CPC .. A61K 35/16; A61K 2035/122; A61K 35/44; A61K 31/00; A61K 38/17; A61K 48/00; C07H 21/04; C07K 14/435; C07K 14/47; C07K 14/575; C12N 5/06; C12N 9/00; C12N 9/64; C12P 21/02; C12Q 1/68
See application file for complete search history.

(56) References Cited

PUBLICATIONS

Newman, M., et al., Cytokines produced by cultured human umbilical cord blood (HUCB) cells; implications for brain repair. Experimental Neurology 199 (2006) 201-208.

*Primary Examiner* — Deborah K Ware
(74) *Attorney, Agent, or Firm* — Michele L. Lawson; Robert J. Varkonyi; Smith & Hopen, P.A.

(57) ABSTRACT

Administration of human umbilical cord blood cells (HUCBC) or HUCBC-derived plasma is used to treat amyloid-based diseases, such as Alzheimer's disease, Huntington's disease, cerebral amyloid antigopathy, and type-II diabetes. Modulating inflammatory reactions by infusing HUCBC resulted in a marked reduction of amyloid plaques and immune-associated cellular damage. HUCBC infusion also significantly reduced cerebral amyloid angiopathy in mice models. These effects were associated with suppression of the CD40-CD40L interaction and a reduction in surface expressed CD-40 was observed on immune cells. Further, Aβ phagocytic activity was increased and soluble and insoluble Aβ protein levels were modulated by treatment. HUCBC-infused sera also significantly increased phagocytosis of $A\beta_{1-42}$ peptide and inhibited immune cell CD40 expression and reduced cerebral amyloid angiopathy.

17 Claims, 14 Drawing Sheets

HUCBC TREATMENT OF AMYLOID-ASSOCIATED DISEASE

CROSS REFERENCE TO RELATED APPLICATIONS

This application is a divisional of prior filed U.S. Nonprovisional application Ser. No. 12/706,510, entitled "HUCBC Treatment of Amyloid Associated Disease", filed Feb. 16, 2010; which is a continuation of prior filed International Application, Serial Number PCT/US2008/073265, entitled "HUCBC Treatment of Amyloid Associated Disease", filed Aug. 15, 2008; which claims priority to U.S. provisional patent application No. 60/956,040, filed on Aug. 15, 2007, the contents of which are herein incorporated by reference.

STATEMENT OF GOVERNMENT INTEREST

This work was made with government support under grant number R41AG031586 awarded by the National Institutes of Health and National Institute on Aging and under grant number R01NS048335 awarded by the National Institutes of Health and the National Institute of Neurological Disorders and Stroke. The government has certain rights in the invention.

FIELD OF INVENTION

This invention relates to amyloid protein-based diseases. Specifically, the invention relates to mediators of amyloid peptide levels, immune responses, and treatments of Alzheimer's disease.

BACKGROUND OF THE INVENTION

Amyloid diseases, such as Alzheimer's disease, Huntington's disease, and type II diabetes, are debilitating diseases resulting from cellularly processed protein agglomerates. Alzheimer's disease (AD) is the most common progressive dementing disorder characterized by deposition of amyloid-β peptide (Aβ) in the brain parenchyma. Aβ plaques are potent activators of both microglia and astrocytes, central nervous system (CNS)-resident immunocompetent cells that respond to cerebral amyloidosis by pro-inflammatory, chronic activation (Bussiere, T., et al., Morphological characterization of Thioflavin-S-positive amyloid plaques in transgenic Alzheimer mice and effect of passive A-beta immunotherapy on their clearance. *Am. I Pathol.* 165: 987-995, 2004).

Studies have suggested that the Aβ-mediated inflammatory cascade not only affects clinical outcomes but also the extent of neuronal injury. Strategies aimed at manipulating this inflammatory cascade, including Aβ immunization (Chen, B., et al., Intravenous administration of human umbilical cord blood reduces behavioral deficits after stroke in rats. *Stroke* 32: 2682-2688, 2001; Ende, N., and I L Chen. Parkinson's disease mice and human umbilical cord blood I *MecL* 33: 173-180, 2002), non-steroidal anti-inflammatory drugs (NSAID) (Cole, G., et al. NSAID and Antioxidant Prevention of Alzheimer's Disease: Lessons from In Vitro and Animal Models. *Ann. N.Y. Acad ScL* 1035: 68-84. 2004; Henning, R., et al. Human umbilical cord blood mononuclear cells for the treatment of acute myocardial infarction. *Cell Transplant.* 13: 729-7392004; Holcomb, L., et al. Accelerated Alzheimer-type phenotype in transgenic mice carrying both mutant amyloid precursor protein and presenilin 1 transgenes. *Nat. Med* 4:97-100, 1998) and modulation of microglial activation (McGowan, E., et al. Amyloid phenotype characterization of transgenic mice overexpressing both mutant amyloid precursor protein and mutant presenilin I transgenes. *Neuroblol. Dis.* 6:231-244, 1999; Newman, M. B., et al. Human umbilical cord blood (HUCB) cells for central nervous system repair. *Neurotoz Res.* 5: 355-368, 2003; Roach, T., et al. Behavioral effects of CD40-CD40L pathway disruption in aged PSAPP mice. *Brain Res.* 1015: 161-168, 2004), are able to reduce AD-like pathology and improve behavioral impairment in Alzheimer's transgenic mouse models and, in some cases, reduce AD pathology in humans.

It was previously shown that the CD40-CD40 ligand (CD40L) interaction plays a critical role in Aβ-induced microglial activation (Tan et al., Microglial activation resulting from CD40-CD40L interaction after beta-amyloid stimulation. *Science,* 286:2352-2355, 1999). Disruption of this signaling pathway reduces cerebral Aβ deposits in Tg2576 mice and improves cognitive deficits in PSAPP mice (Tan et al., CD40-CD40L interaction in Alzheimer's disease. *Curr Opin Pharmacol,* 2:445-451, 2002; Roach et al., Behavioral effects of CD40-CD40L pathway disruption in aged PSAPP mice. *Brain Res,* 1015:161-168, 2004). The implication of the CD40-CD40L interaction in AD-associated brain inflammatory processes is supported from studies demonstrating increased expression of CD40 and CD40L in and around the β-amyloid plaques characteristic of the AD brain (Togo, et al., Expression of CD40 in the brain of Alzheimer's disease and other neurological diseases, *Brain Res,* 885:117-121, 2000; Calingasan, et al., Identification of CD40 ligand in Alzheimer's disease and in animal models of Alzheimer's disease and brain injury. *Neurobiol Aging,* 23:31-39, 2002). Recently, Desideri and colleagues (Desideri G., et al., Enhanced soluble CD40 ligand and Alzheimer's disease: evidence of possible pathogenetic role. *Neurobiol Aging,* 29:348-356, 2007) reported that circulating soluble CD40L (sCD40L) levels are significantly increased in AD patients versus healthy elderly controls, further suggesting an important association between CD40-CD40L interactions and the pathogenesis of AD.

Human umbilical cord blood cells (HUCBC) have been shown to be antagonists of the pro-inflammatory T helper cell type 1 (Th1) response, as demonstrated in an animal model of stroke where HUCBC infusion promoted a strong T-helper 2 (Th2) response (Vendrame, M., et al., Infusion of human umbilical cord blood cells in a rat model of stroke dose-dependently rescues behavioral deficits and reduced infarct volume. *Stroke,* 35:2390-2395, 2004). This modulation was correlated with reduced infarct volume and a rescue of behavioral deficits (Vendrame 2004). HUCBC infusion has also shown to be a therapeutic benefit in other neuroinflammatory conditions including multiple sclerosis, amyotrophic lateral sclerosis, neurodegenerative macular degeneration, and Parkinson's disease (Henning, R., et al. Human umbilical cord blood progenitor cells are attracted to infracted myocardium and significantly reduce myocardial infarction size. *Cell Transplant.* 15: 647-658, 2004; Garbuzaova-Davis S., et al., Maternal transplantation of human umbilical cord blood cells provides prenatal therapy in Sanfilippo type B mouse model. *FASEB J.,* 20:485-487, 2006). In AD preclinical models, administration of these cells into PSAPP mice was associated with life extension, although high doses were administered (Ende, N. et al, Human umbilical cord blood cells ameliorate Alzheimer's disease in transgenic mice. *J Med,* 32:241-247, 2001).

Modulation of the inflammatory cascade by several diverse strategies including Aβ immunization, non-steroidal anti-inflammatory drug (NSAID) administration, and manipulation of microglial activation states have all been shown to reduce Alzheimer disease (AD)-like pathology, and cognitive deficits in AD transgenic mouse models. However, these treatments also possess strong side effects, for example an increased risk of bleeding associated with NSAID use. Therefore, a safer, efficacious AD treatment is needed.

SUMMARY OF THE INVENTION

Administration of biological composition of human umbilical cord blood cells or plasma treated with human umbilical cord blood cells to AD transgenic mouse models was investigated to determine in vivo effects of HUCBC on AD-like pathology. Double transgenic PSAPP mice and Tg2576 mice were infused with HUCBC or plasma treated with human umbilical cord blood cells and then examined for changes in cerebral Aβ levels/deposits, astrocytosis, microgliosis, cerebral amyloid antigopathy (CAA), and association with the disruption of CD40 signaling pathway.

HUCB cells can be administered as whole cell extracts or a substantially purified mononuclear cell fraction. HUCBC were administered peripherally, administering multiple low doses as this administration method appears to be superior to a single high dose treatment in reducing Aβ burden. However, both methods of administration are envisioned. In some embodiments, the biological composition is administered at or before the occurrence of visible beta-amyloid deposits.

CD40-CD40 ligand (CD40L) interaction was found to play an important role in Aβ-induced microglial activation and disruption of this signaling pathway reduces cerebral Aβ deposits in Tg2576 mice and improves cognitive deficits in PSAPP mice. Further supporting these findings Desideri and colleagues (2007) reported circulating soluble CD40L (sCD40L) levels are significantly increased in AD patients (40 healthy subjects and 77 AD cases), suggesting an important association between CD40-CD40L interactions and the pathogenesis of AD.

The biological composition were administered to AD transgenic mouse models to investigate potential AD-like pathology reduction through suppression of CD40 signaling. In this regard, both double transgenic PSAPP mice and Tg2576 mice were infused with HUCBC or plasma treated with human umbilical cord blood cells and then examined for changes in cerebral Aβ levels/deposits, astrocytosis, microgliosis, cerebral amyloid antigopathy (CAA), and association with the disruption of CD40 signaling pathway. In some embodiments, administering the biological composition modulates the phagocytic activity of microglia, macrophages, and astrocytes, allowing control over the inflammatory response to Aβ. In concert with this down-regulation of pro-inflammatory signaling cultured microglia isolated from HUCBC-infused PSAPP mice demonstrated increased Aβ phagocytic activity. This was further exemplified by sera from HUCBC-infused PSAPP mice which significantly increased microglial phagocytosis of $A\beta_{1-42}$ peptide while inhibiting IFN-γ induced microglial CD40 expression. Moreover this upregulation of microglial phagocytic activity was inhibited by addition of recombinant CD40L protein, evidencing that alterations to cytokine levels, modulate the immune response pathways.

In alternative embodiments, administering the biological compositions into PSAPP mice resulted in a marked reduction of Aβ/β-amyloid plaques and associated astrocytosis. HUCBC infusion also significantly reduced cerebral amyloid angiopathy in Tg2576 mice. Importantly, these effects were associated with suppression of the CD40-CD40L interaction as evidenced by decreased serum CD40L levels and attenuated CD40L-induced inflammatory responses. Immunochemical staining and Western blot analyses confirmed a reduction in surface expression of microglial CD40 as well. It was also observed that Aβ/β-amyloid loads were reduced by either crossing Tg2576 mice with CD40L null mice or treating PSAPP mice with CD40L antibody, these data suggest that HUCBC infusion confers a mitigation of AD-like pathology by disrupting CD40L activity. Moreover, administering the biological compositions to Tg2576 mice or PSAPP mice also disrupted CD40L activity and resulted in reduced Aβ plaque burdens and increased plasma Aβ levels.

The treatment methods discussed above are effective at treating and preventing amyloid diseases, including Alzheimer's Disease, Huntington's Disease, and type II diabetes.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
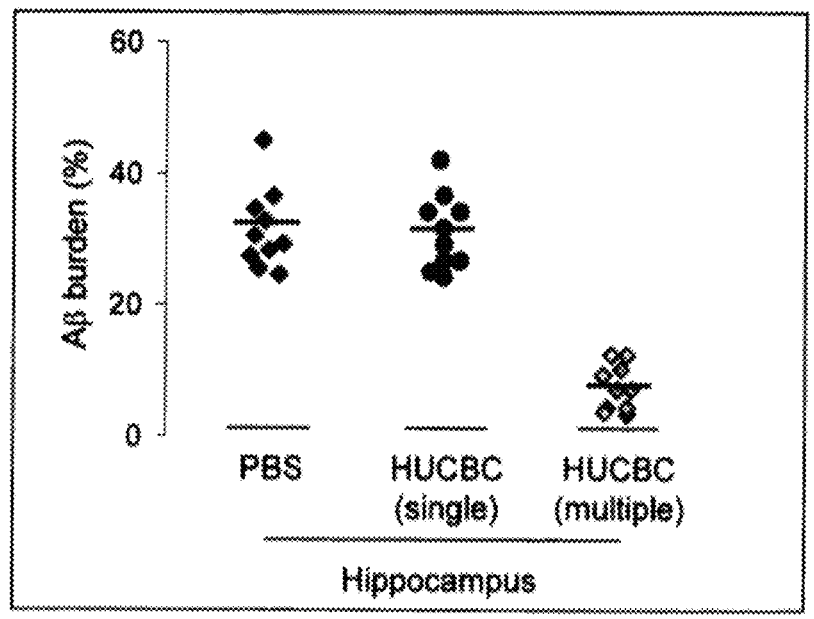
FIG. 1 is a graph of Aβ treatment in PSAPP mice. Mice were treated with PBS (control), a single dose of HUCBC at $1 \times 10^6$ cells/mouse, or multiple doses of HUCBC at $1 \times 10^5$ biweekly for the first 2 months and bi-monthly for the remaining 4 months. The resulting Aβ burden was classified for each treatment.

"Patient" is used to describe an animal, preferably a human, to whom treatment is administered, including prophylactic treatment with the compositions of the present invention.

The term "umbilical cord blood" or "cord blood" is used to refer to blood from a neonate or fetus, preferably neonatal blood obtained from the umbilical cord or placenta of newborns. The use of blood as a source of mononuclear cells is advantageous due to the relative ease of collection.

The "therapeutically effective amount" for purposes herein is thus determined by such considerations as are known in the art. A therapeutically effective amount of the umbilical cord cells, umbilical cord cell-derived plasma, or any combination thereof is that amount necessary to provide a therapeutically effective result in vivo. The amount of umbilical cord cells, umbilical cord cell-derived plasma, or any combination thereof must be effective to achieve a response, including but not limited to total prevention of (e.g., protection against) and to improved survival rate or more rapid recovery, or improvement or elimination of symptoms associated with neurodegenerative disorders (such as ALS), neural damage, or other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration.

"Umbilical cord cell-derived plasma" means plasma isolated from the blood of an animal wherein umbilical cord cells were administered. As used herein, the umbilical cord cell-derived plasma was collected after the umbilical cord cells were given adequate time to elicit a response from the animal.

"Administration" or "administering" is used to describe the process in which umbilical cord cells, umbilical cord cell-derived plasma, or any combination thereof of the present invention are delivered to a patient. The composition may be administered in various ways including parenteral (referring to intravenous and intraarterial and other appropriate parenteral routes), intratheceal, intraventricular, intracisternal, intranigral, among others. Each of these conditions may be readily treated using other administration routes of whole umbilical cord blood, a mononuclear fraction thereof, or umbilical cord cell-derived plasma to treat a disease or condition.

The term "essentially" is used to describe a population of cells or a method that is at least 90% purified, preferably at least 95% purified, and more preferably 98+% purified. Cells according to the present invention are preferably essentially free of hematopoeitic cells, i.e. CD 34 positive cells fractions.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pa., Mack Publishing Company, 19$^{th}$ ed.) describes formulations which can be used in connection with the subject invention.

Data are presented as mean±SD. All statistics were analyzed using a one-way multiple-range analysis of variance test (ANOVA) for multiple comparisons. A value of $p<0.05$ was considered significant.

Figure 2:
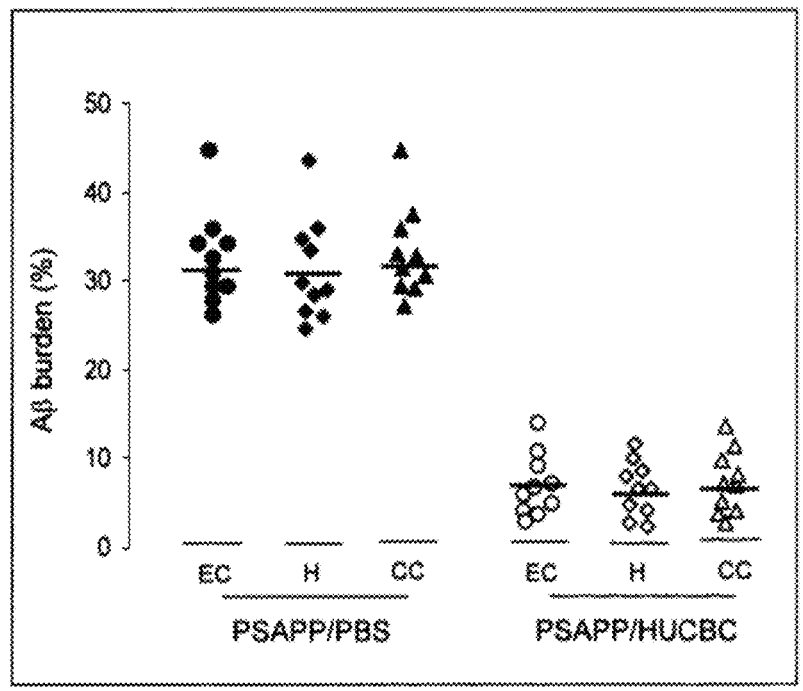
FIG. 2 shows a graph indicating cerebral Aβ/β-amyloid pathology is reduced in PSAPP and Tg2576 mice peripherally infused with HUCBC (PSAPP/HUCBC). Mouse paraffin-embedded coronal brain sections from the cingulate cortex (CC), hippocampus (H), and entorhinal cortex (EC) stained with monoclonal human Aβ antibody, 4G8. Percentages (plaque area/total area) of Aβ antibody-immunoreactive deposits were calculated by quantitative image analysis (mean±SD; n 10, 5 females and 5 males per group).
Figure 3:
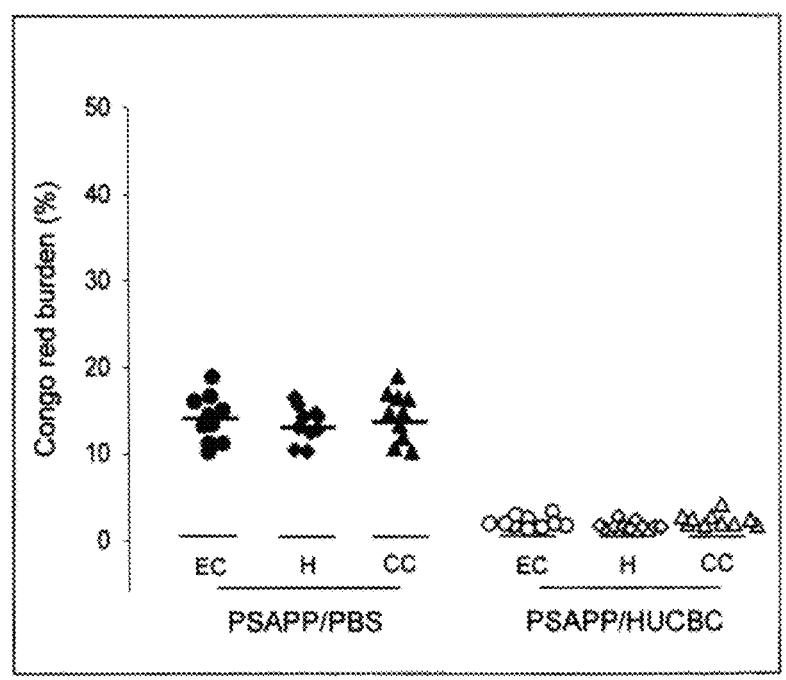
FIG. 3 shows a graph indicating cerebral Aβ/β-amyloid pathology is reduced in PSAPP and Tg2576 mice peripherally infused with HUCBC (PSAPP/HUCBC). Mouse paraffin-embedded coronal brain sections from the cingulate cortex (CC), hippocampus (H), and entorhinal cortex (EC) stained with Congo red. Percentages (plaque area/total area) of Congo red-stained sections were calculated by quantitative image analysis (mean±SD; n 10, 5 females and 5 males per group).
Figure 4A:
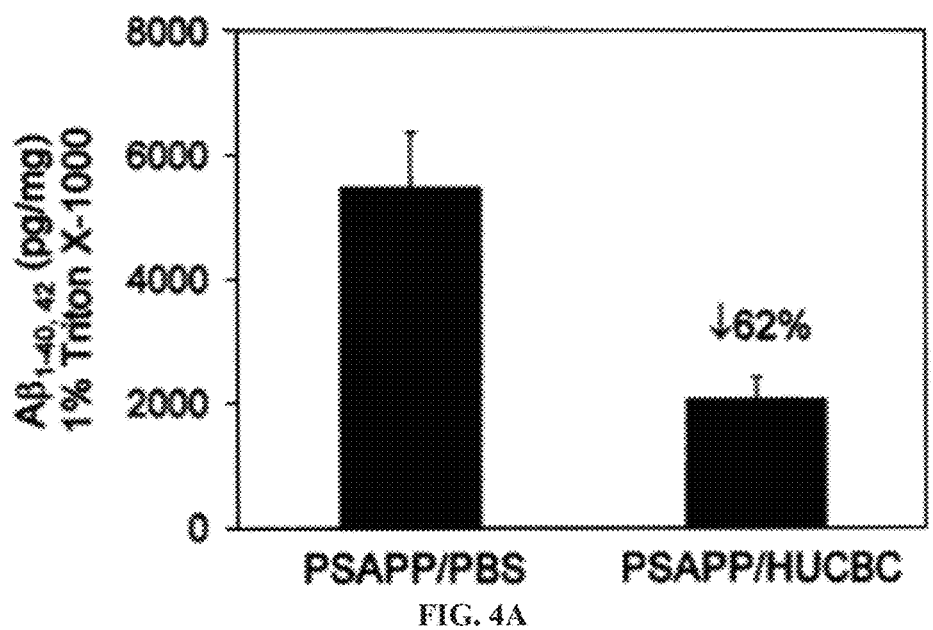
FIG. 4A shows a graph indicating cerebral Aβ/β-amyloid pathology is reduced in PSAPP and Tg2576 mice peripherally infused with HUCBC (PSAPP/HUCBC). A EUSA analysis was carried out for both levels of detergent-soluble $A\beta_{1-40, 42}$. Data are represented as mean±SD of $A\beta_{1-40, 42}$ (pg/mg protein). No significant difference was observed in cerebral Aβ-amyloid deposits between adult human mononuclear cells and PBS peripherally infused PSAPP mice (data not shown).
Figure 4B:
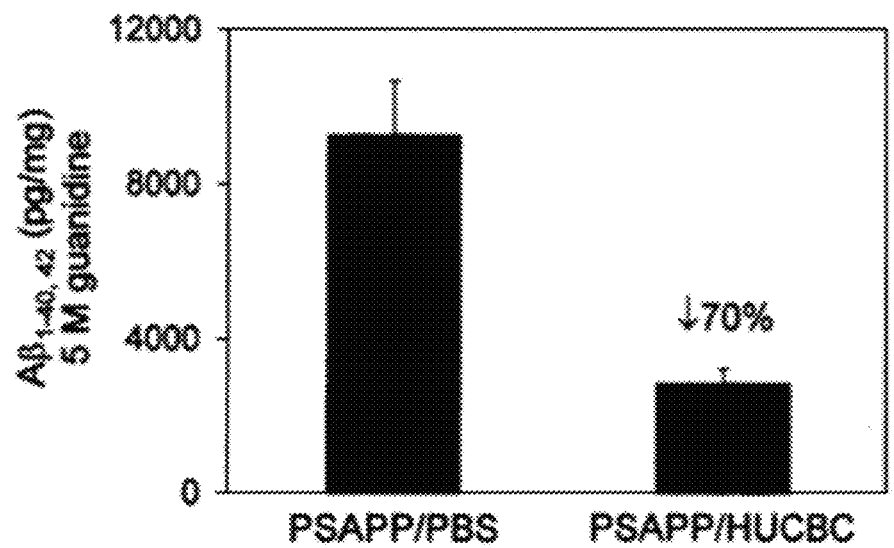
FIG. 4B shows a graph indicating cerebral Aβ/β-amyloid pathology is reduced in PSAPP and Tg2576 mice peripherally infused with HUCBC (PSAPP/HUCBC). A EUSA analysis was carried out for 5 M guanidine-extracted $A\beta_{1-40, 42}$ (bottom panel). Data are represented as mean±SD of $A\beta_{1-40, 42}$ (pg/mg protein). No significant difference was observed in cerebral Aβ-amyloid deposits between adult human mononuclear cells and PBS peripherally infused PSAPP mice (data not shown).

Cerebral β-amyloid plaques/angiopathy are reduced in both of PSAPP and Tg2576 AD transgenic mice peripherally infused with HUCBC HUCBC (95-98% mononuclear cells) were administered to PSAPP double transgenic mice to determine whether HUCBC infusion impacts Aβ-associated pathology. HUCBC treatment conditions were evaluated against resulting Aβ peptide burden for a single, high dose administration of 1,000,000 cells/mouse versus multiple low dose administrations of 100,000 cells/mouse biweekly for the first 2 months and bimonthly for the remaining 4 months, as seen in FIG. 1. The PSAPP mice were intravenously (iv) injected beginning at 7 months of age with 100,000 HUCBC cells/mouse biweekly for the first 2 months and bimonthly for the remaining 4 months. This corresponds with the occurrence of visible histological β-amyloid deposit formation. At 13 months of age, mice were sacrificed and evaluated for changes in AD-like pathology. Aβ antibody (4G8) immunohistochemistry, (data not shown) and Congo Red histochemistry (data not shown) evidence the markedly reduced cerebral β-amyloid pathology of HUCBC-infused PSAPP mice compared to control. Quantitative t-test image analysis for independent samples analysis revealed significant differences for each brain region examined between PSAPP mice infused with HUCBC (PSAPP/HUCBC) compared to PSAPP mice peripherally infused with PBS (PSAPP/PBS) for both Aβ antibody and Congo red staining (P<0.001; FIGS. 2 and 3, respectively). Furthermore, ELISA assay showed brain levels of both detergent-soluble and -insoluble $A\beta_{1-40, 42}$ peptides were reduced in PSAPP mice infused with HUCBC (62% and 70%, respectively), as seen in FIGS. 4(A) and (B). A t-test for independent samples revealed significant differences between groups for each group examined (P<0.001).

Figure 5A:
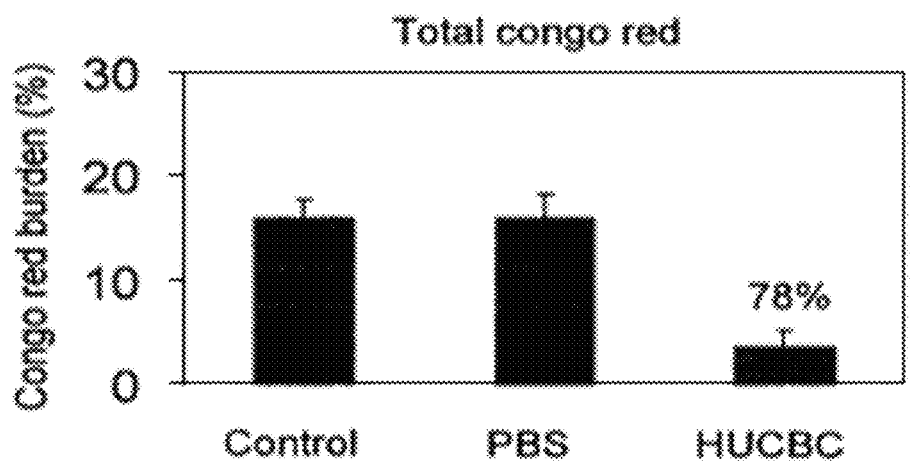
FIG. 5A shows a graph indicating total cerebral Aβ/β-amyloid pathology is reduced in PSAPP and Tg2576 mice peripherally infused with HUCBC (PSAPP/HUCBC). Mouse paraffin-embedded coronal brain sections from the hippocampal regions were stained with Congo red. Percentages (% of area) of Congo red-stained plaque vessels were quantified by image analysis (mean±SD; n=10, 5/5c). A percentage of reduction is indicated.
Figure 5B:
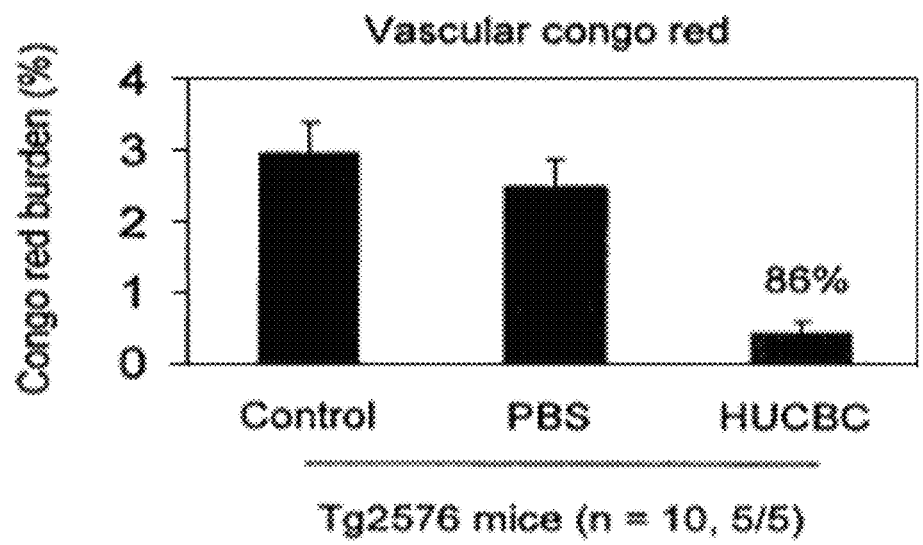
FIG. 5B shows a graph indicating vascular cerebral Aβ/β-amyloid pathology is reduced in PSAPP and Tg2576 mice peripherally infused with HUCBC (PSAPP/HUCBC). Mouse paraffin-embedded coronal brain sections from the hippocampal regions were stained with Congo red. Percentages (% of area) of Congo red-stained plaque vessels were quantified by image analysis (mean±SD; n=10, 5/5c). A percentage of reduction is indicated.
Figure 5C:
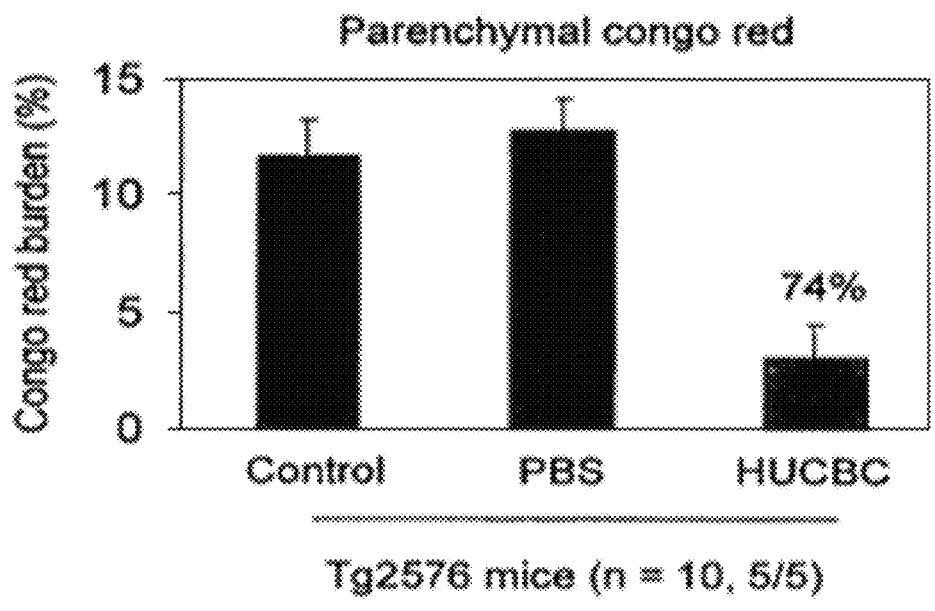
FIG. 5C shows a graph indicating total parenchymal Aβ/β-amyloid pathology is reduced in PSAPP and Tg2576 mice peripherally infused with HUCBC (PSAPP/HUCBC). Mouse paraffin-embedded coronal brain sections from the hippocampal regions were stained with Congo red. Percentages (% of area) of Congo red-stained plaque vessels were quantified by image analysis (mean±SD; n=10, 5/5c). A percentage of reduction is indicated.

The effects of HUCBC on cerebral amyloid angiopathy (CAA) were examined in Tg2576 mice, given that peripherally administered HUCBC reduces cerebral Aβ levels/Aβ deposits in PSAPP mice. CAA is known to occur in approximately 83% of AD patients and is characterized by A deposits in the cerebral vasculature. Tg2576 mice were used as an AD model, as the mice manifest copious amounts of A deposits in cerebral vessels at 15-20 months of age (Christie, R., et al., Structural and functional disruption of vascular smooth muscle cells in a transgenic mouse model of amyloid angiopathy, *Am J Pathol*, 158:1065-1071, 2001; Li, L., et al., Association of aortic athersclerosis with cerebral beta-amyloidosis and learning deficits in a mouse model of Alzheimer's disease, *Am J Pathol*, 163:2155-2164, 2003). The mice were peripherally infused with HUCBC, PBS, or without treatment (n=10, 5♂/5♀ per group) at 12 months of age using an identical procedure. Six months thereafter, the mice were sacrificed for analysis of cerebral parenchyal or vascular β-amyloid deposits/angiopathy by Congo Red histochemistry. Tg2576 mice receiving HUCBC treatment demonstrated reduction in cerebral parenchymal and vascular Congo Red deposits compare to controls, (data not shown). This is notably shown in the hippocampus for Tg2576 mice receiving HUCBC or PBS infusion. Quantitative t-test image analysis for independent samples revealed significant differences between Tg2576/HUCBC and Tg2576/PBS or nontreated control groups (P<0.001; FIGS. 5(A)-(C)) when total (78%), parenchymal (74%), or vascular (86%) Congo red staining was examined. However, no significant difference was revealed between PSAPP/PBS and PSAPP control mice (P>0.05). Cerebral Aβ levels/β amyloid deposits were also analyzed using Aβ ELISA and Aβ antibody immunochemistry staining for these three groups. Similar to the effects observed in HUCBC-infused PSAPP mice, Tg2576 mice infused with HUCBC displayed a marked decrease in cerebral soluble/insoluble Aβ levels and β-amyloid loads comparable to PBS-infused or control Tg2576 mice (P<0.001; data not shown).

Figure 6:
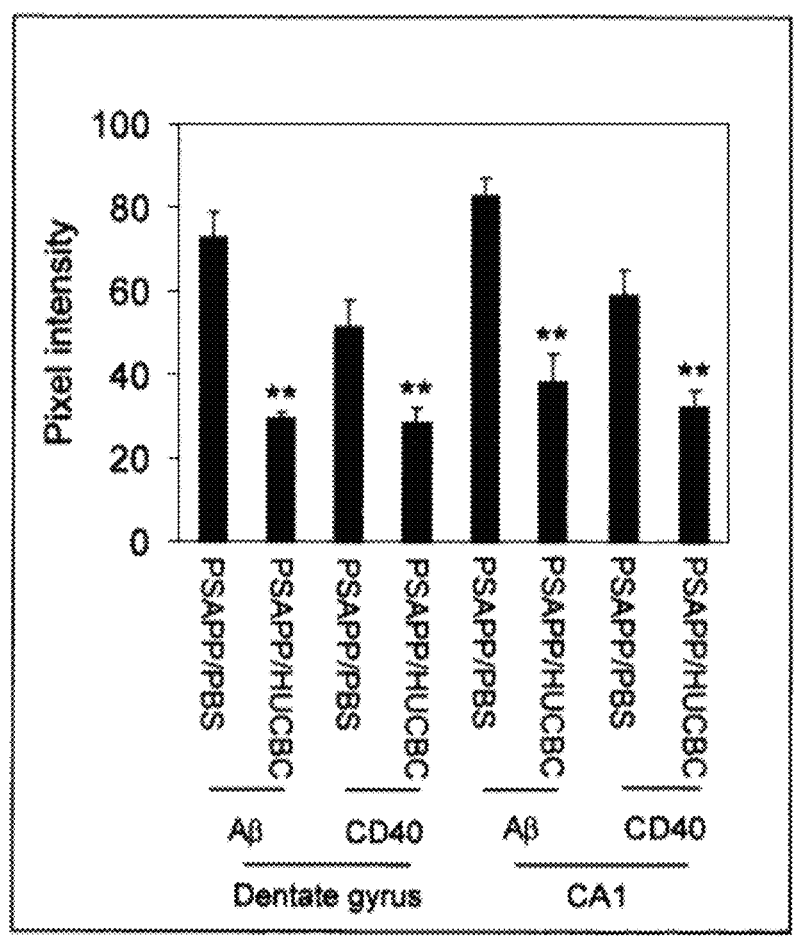
FIG. 6 is a graph indicating β-amyloid associated microgliosis and astrocytosis are reduced in HUCBC peripherally infused-PSAPP mice. Immunofluorescent staining analysis was performed on mouse brain coronal paraffin sections prepared from PSAPP/HUCBC-infused and PSAPP/PBS-infused mice. Intensity representation of the Aβ and CD40 images was carried out using the Statistical Package for the Social Sciences release 10.0.5 (SPSS, Inc., Chicago, Ill.).
Figure 7:
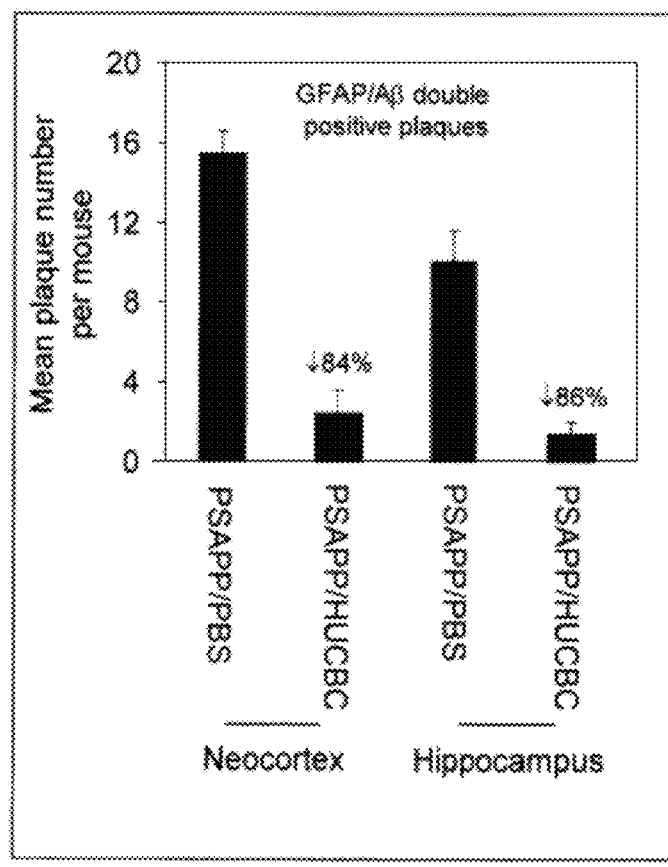
FIG. 7 is a graph indicating β-amyloid associated microgliosis and astrocytosis are reduced in HUCBC peripherally infused-PSAPP mice. Densitometty analysis of Western blotting using anti-mouse CD40 antibody the ratio of CD40 to actin indicated below the figure. Immunochemistry analysis shows 4G8 and GFAP staining and immunofluorescent GFAP/Aβ staining reveals co-localization of GFAP and Aβ. Morphometric analysis results (mean GFAP/β-amyloid double positive plaques per mouse±SD) are shown for the neocortex and the hippocampus as indicated. Percent reduction of double positive plaques in PSAPP/HUCBC-infused mice is indicated.

Reduced CD40+ Microgliosis and GFAP+ Astrocytosis in PSAPP Mice Peripherally Infused with HUCBC Microgliosis and astrocytosis-associated inflammatory responses are believed to contribute to β-amyloid plaque formation. Ligation of microglial CD40 enables activation in response to Aβ peptides. β-amyloid deposits were examined in PSAPP mice for colocalization with CD40+ microglia or reactive GFAP+ astrocytes to determine whether HUCBC could inhibit inflammation, using both histochemistry staining and Western blot analyses. CD40+ microglial cells were reduced in the PSAPP/HUCBC-infused group, (data not shown). Quantitative t-test for independent samples revealed significant differences between PSAPP/HUCBC-infused and PSAPP/PBS-infused groups (**P<0.001) for hippocampal dentate gyrus and CA1 regions, seen in FIG. 6. Western blot analysis also showed a marked decrease in CD40 expression in brain homogenates from HUCBC-infused PSAPP mice (P<0.001 with n=5; data not shown). Furthermore, immunochemistry/histochemistry and immunofluorescence analyses showed markedly reduced β-amyloid-associated astrocytosis in PSAPP/HUCBC mice (P<0.001; data not shown). A t-test for independent samples revealed a significant reduction of double positive plaques in PSAPP/HUCBC-infused mice for neocortex and hippocampus by 84% and 86%, respectively when compared to PSAPP/PBS-infused mice (P<0.001 for each comparison) using the morphometric analysis, seen in FIG. 7.

Figure 8:
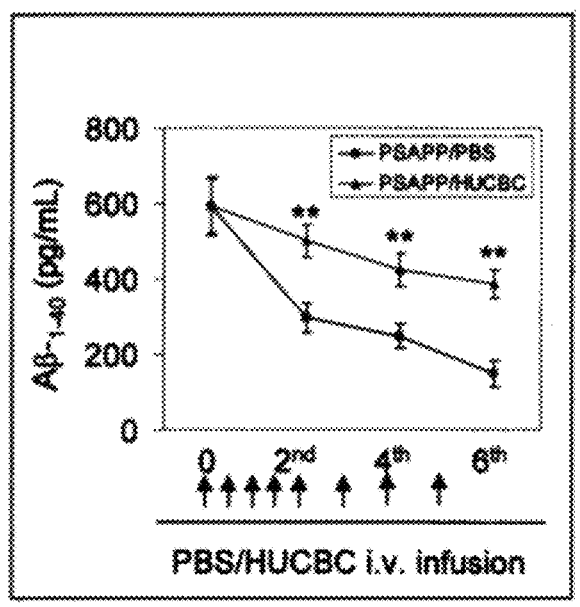
FIG. 8 is a graph showing HUCBC infusion results in increased plasma Aβ levels and decreased CD40 signaling pathway in PSAPP mice. ELISA analysis shows plasma $A\beta_{1-40}$. Data are presented as mean (±SD; n 10) of $A\beta_{1-40}$ (pg/mL plasma). Arrows below the panels show the time for each peripheral infusion with HUCBC or PBS. ELISA is shown for plasma-derived treatment.
Figure 9:
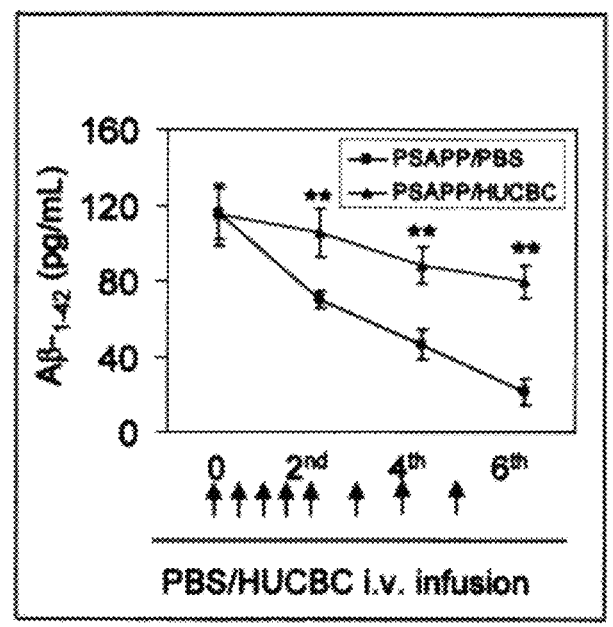
FIG. 9 is a graph showing HUCBC infusion results in increased plasma Aβ levels and decreased CD40 signaling pathway in PSAPP mice. ELISA analysis shows placma $A\beta_{1-42}$ peptides presented as mean (±SD; n 10) of $A\beta_{1-40}$ (pg/mL plasma). Arrows below the panels show the time for each peripheral infusion with HUCBC or PBS.
Figure 10:
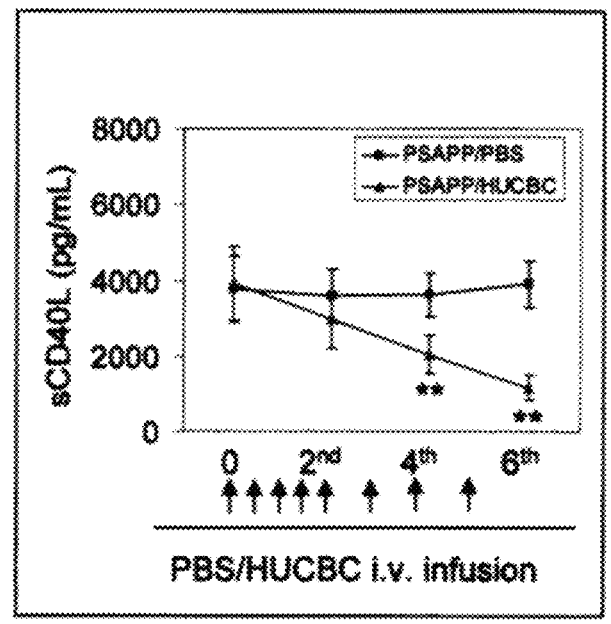
FIG. 10 is a graph showing HUCBC infusion results in increased plasma Aβ levels and decreased CD40 signaling pathway in PSAPP mice. ELISA analysis shows plasma sCD40L presented as mean (±SD; n 10) of sCD40L (pg/mL plasma). Arrows below the panels show the time for each peripheral infusion with HUCBC or PBS.
Figure 11:
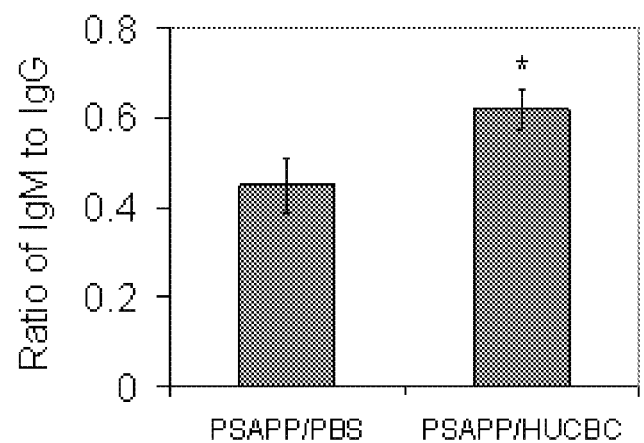
FIG. 11 is a graph showing HUCBC infusion results in increased plasma Aβ levels and decreased CD40 signaling pathway in PSAPP mice. ELISA analysis shows plasma IgM/IgG presented as mean (±SD; n 10) of Data are presented as a ration of IgM to IgG in blood from mice at the 6th month following the treatment.
Figure 12:
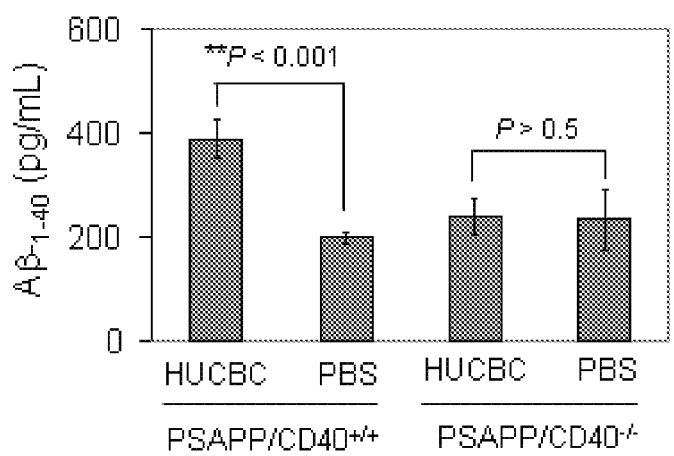
FIG. 12 is a graph showing HUCBC infusion results in increased plasma Aβ levels and decreased CD40 signaling pathway in PSAPP mice. Aβ ELISA analysis of $A\beta_1$-40 in plasma derived from PSAPP/CD40$^{+/+}$ or PSAPP/CD40$^{-/-}$ mice at the 2d month, following the third HUCBC infusion. Data are presented as a mean±SD (n=4, 2 males and 2 females) of $A\beta_{1-40}$ (pg/mL plasma).
Figure 13:
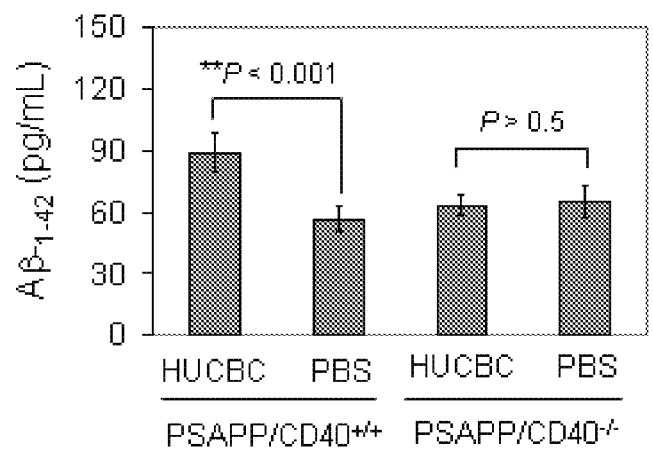
FIG. 13 is a graph showing HUCBC infusion results in increased plasma Aβ levels and decreased CD40 signaling pathway in PSAPP mice. Aβ ELISA analysis of $A\beta_{1-42}$ in plasma derived from PSAPP/CD40$^{+/+}$ or PSAPP/CD40$^{-/-}$ mice at the 2d month, following the third HUCBC infusion. Data are presented as a mean±SD (n=4, 2 males and 2 females) of $A\beta_{1-42}$ (pg/mL plasma).

Increased Plasma Aβ Levels Correlate with Decreased CD40-CD40L Interaction in HUCBC-Infused PSAPP Mice Administration of neutralizing CD40L antibody to PSAPP mice results in increased levels of plasma Aβ concomitant with reduced cerebral Aβ/β-amyloid pathology, suggesting that depletion of CD40L promotes brain-to-blood clearance of Aβ (Tan, J., 2002). CD40-CD40L is known to promote proinflammatory Th2 while opposing anti-inflammatory Th2 responses (Grewal, I. and Flavell, R., CD40 and CD154 in cell-mediated immunity. *Ann Rev Immunol*, 16:111-135, 1998; Mackey, M., et al., The role of CD40/CD154 interactions in the priming, differentiation, and effector function of helper and cytotoxic T cells. *J Leukoc Biol*, 63:418-428, 1998). Further, HUCBC treatment is an immunoregulator in animal models of stroke and other neurodegenerative disorders (Vendrame, M., 2004; Newman, M., et al., Cytokines produced by cultured human umbilical cord blood (HUCB) cells: implications for brain repair. *Exp Neurol*, 199:201-208, 2006). The method of Aβ level/β-amyloid deposit reduction was investigated for HUCBC-infused PSAPP mice, focusing on possible brain-to-blood clearance and suppression of pro-inflammatory CD40-CD40L interaction. Individual blood samples were collected from PSAPP mice infused with HUCB cells or PBS for $A\beta_{1-40, 42}$ and sCD40L. ELISA assay revealed increased plasma $A\beta_{1-40, 42}$ levels in PSAPP/HUCBC mice, inversely correlating with decreased levels of plasma sCD40L in these animals, seen in FIGS. 8-10. One-way ANOVA followed by post hoc comparison revealed significant differences between PSAPP/HUCBC-infused and PSAPP/PBS infused mice for both plasma $A\beta_{1-40, 42}$ levels and plasma sCD40L levels, as seen in FIGS. 11-13 (** P<0.001). As CD40-CD40L is required by B cells for IgM to IgG class switching, the interaction between CD40-CD40L suppression and IgM and Ig titers was examined in mouse blood samples at sacrifice. ELISA data showed a significant increase in IgM to IgG in PSAPP/HUCBC mice compared to control, as seen in FIG. 11 (* P<0.05). The results suggest CD40 signalling pathways are functionally suppressed in HUCBC-infused PSAPP mice. CD40 deficiency in APP transgenic mice was found to decrease Aβ/β-amyloid load. Similarly, PSAPP/CD40$^{-/-}$ mice, and to a lesser extent PSAPP/CD40$^{+/+}$ mice, manifest β-amyloid deposits (data not shown). HUCBC cells or PBS was administered to PSAPP/CD40$^{-/-}$ mice at 8 weeks of age and circulating Aβ levels examined, which correlate with cerebral amyloid levels in transgenic AD mice (DeMattos, R., et al., Brain to plasma amyloid-beta efflux: a measure of brain amyloid burden in a mouse model of Alzheimer's disease. *Science*, 295:2264-2267, 2002). There appears to be no added benefit of HUCBC in PSAPP/CD40$^{-/-}$ mice with regard to enhanced Aβ plasma levels, a presumed indicator of Aβ brain-to-blood efflux, as seen in FIGS. 12 and 13

(P<0.05). The data suggest HUCB cells mediate a beneficial effect on reducing amyloidosis by reducing CD40 pathway bioactivity.

Figure 14:
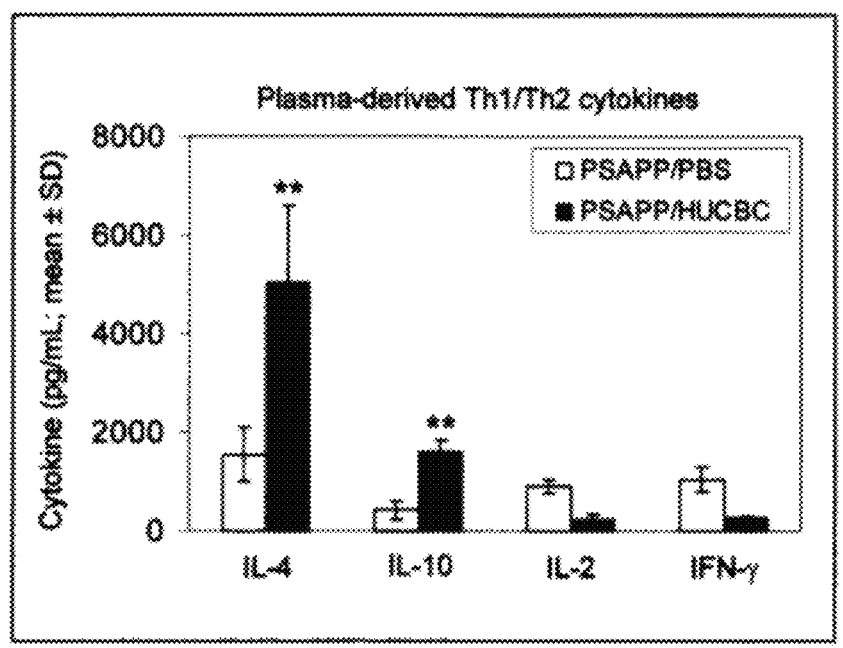
FIG. 14 is a graph showing HUCBC infusion promoted anti-inflammatory/Th2 responses and decreased sCD40L in the CNS. ELISA analysis results are shown for plasma-derived sCD40L. Data are presented as a mean±SD (n=10), 2 males and 2 females) values of cytokines (pg/mL plasma or medium).
Figure 15:
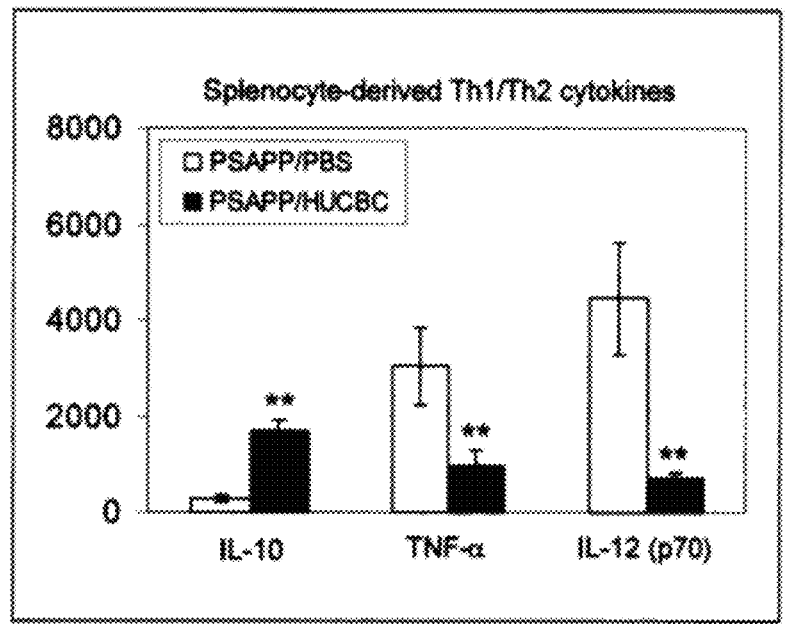
FIG. 15 is a graph showing HUCBC infusion promoted anti-inflammatory/Th2 responses and decreased sCD40L in the CNS. ELISA analysis results are shown for splenocyte-derived sCD40L. Data are presented as a mean±SD (n=10), 2 males and 2 females) values of cytokines (pg/mL plasma or medium).
Figure 16:
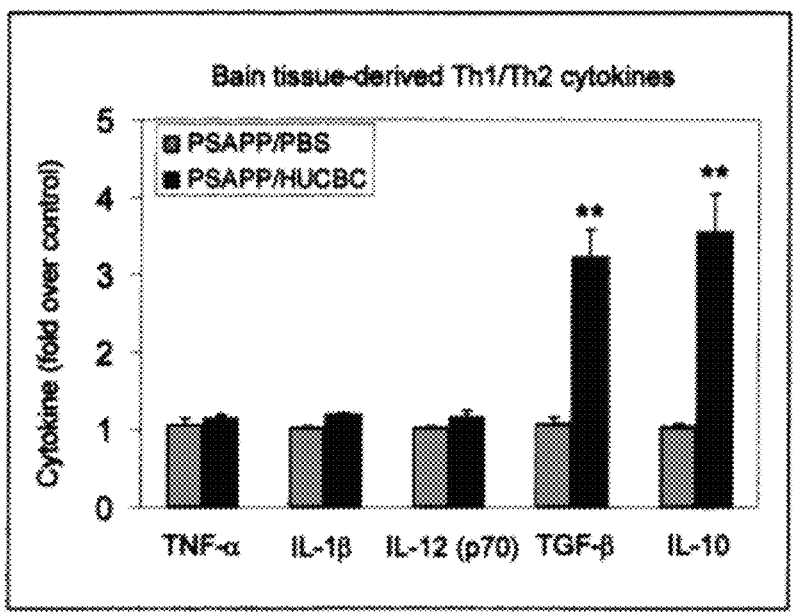
FIG. 16 is a graph showing HUCBC infusion promoted anti-inflammatory/Th2 responses and decreased sCD40L in the CNS. ELISA analysis results are shown for brain tissue-derived cytokines. Data are presented as a fold increase of cytokines over control (untreated) mice.
Figure 17:
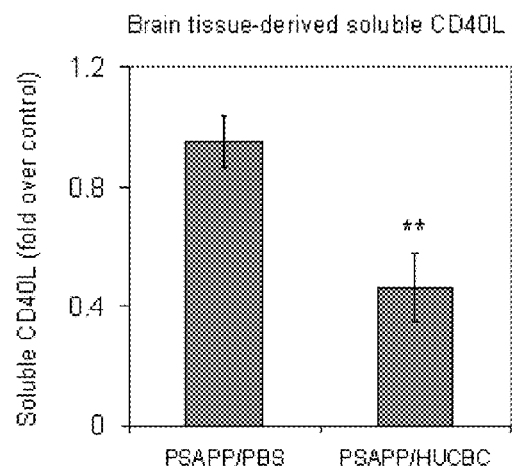
FIG. 17 is a graph showing HUCBC infusion promoted anti-inflammatory/Th2 responses and decreased sCD40L in the CNS. ELISA analysis results are shown for brain tissue-derived sCD40L. Data are presented as a fold increase of cytokines over control (untreated) mice.

Cytokine levels were examined after HUCBC administration to determine if HUCBC-mediated amyloidosis reduction utilizes the CD40 pathway. If this is indeed true, HUCBC treatment should be accompanied by a shift from pro- to anti-inflammatory cytokines. Blood samples were individually collected from PSAPP mice infused with HUCBC or PBS. ELISA revealed increased plasma $A\beta_{1-40, 42}$ which correlated with decreased levels of plasma sCD40L. One-way ANOVA followed by post hoc comparison revealed significant differences between PSAPP/HUCBC-infused and PSAPP/PBS-infused mice for plasma $A\beta_{1-40,42}$ levels and as well as plasma sCD40L levels at each time point indicated (P<0.001). To evaluate the consequence of HUCBC-mediated suppression of CD40 signaling pathway, blood and spleen were assayed for cytokine profiles. As shown in FIGS. 14 and 15, plasma IL-4 and IL-10 increased in HUCBC-infused PSAPP mice. Primary splenocytes from HUCBC-infused PSAPP mice showed reduced TNF-α/IL-12 (p70) and increased IL-10 secretion. Further, ELISA showed CNS cytokine levels markedly increased in TGF-β and IL-10 levels in PSAPP/HUCBC-infused mouse brain homogenates, seen in FIG. 16. A t-test for independent samples showed significant differences between PSAPP/HUCBC- and PSAPP/PBS-infused mice for all cytokines, including plasma IL-4 and IL-10; splenocyte-derived TNF-α/IL-12 (p70) and IL-10; and brain tissue-derived TGF-β and IL-10 (P<0.001). These findings correlate to a dramatic increase in brain-tissue derived sCD40-L, seen in FIG. 17.

Figure 18:
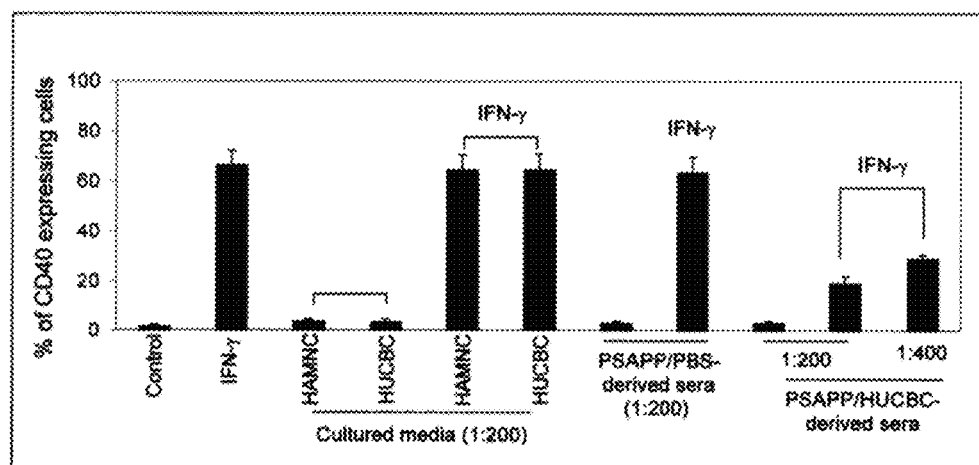
FIG. 18 is a graph showing HUCBC modulate microglial CD40 expression and promote Aβ microglial phagocytic activity. FACS analysis for CD40 expression in primary microglial cells treated with various conditions following IFN1 challenge. Data are presented as percentage of CD40 expressing cells (mean±SD; n=5).

HUCBCs Inhibit Microglial CD40 Expression and Enhances Microglial Phagocytosis of Aβ Peptides CD40 signaling is critically involved in microglia-related inflammatory responses in the CNS and IFN-γ strongly induces microglial CD40 expression. Primary microglial cells were treated with cultured media from HUCBC and control cultures, or serum from HUCBC- or PBS-infused PSAPP mice in the presence of IFN-γ (100 ng/mL) to investigate HUCBC ability to modulate microglial CD40 signaling. After 8 hours, CD40 expression was then examined by FACS analysis. Sera derived from HUCBC-infused PSAPP mice significantly inhibited IFN-γ-induced microglial CD40 expression compared to controls (P<0.001), as shown in FIG. 18. However, this effect is not directly mediated by HUCBC or human adult mononuclear cells (HAMNCs), but likely a secondary effect due to soluble circulating endogenous CD40 regulators produced normally by the immune system in response to the HUCBC infusion.

Figure 19A:
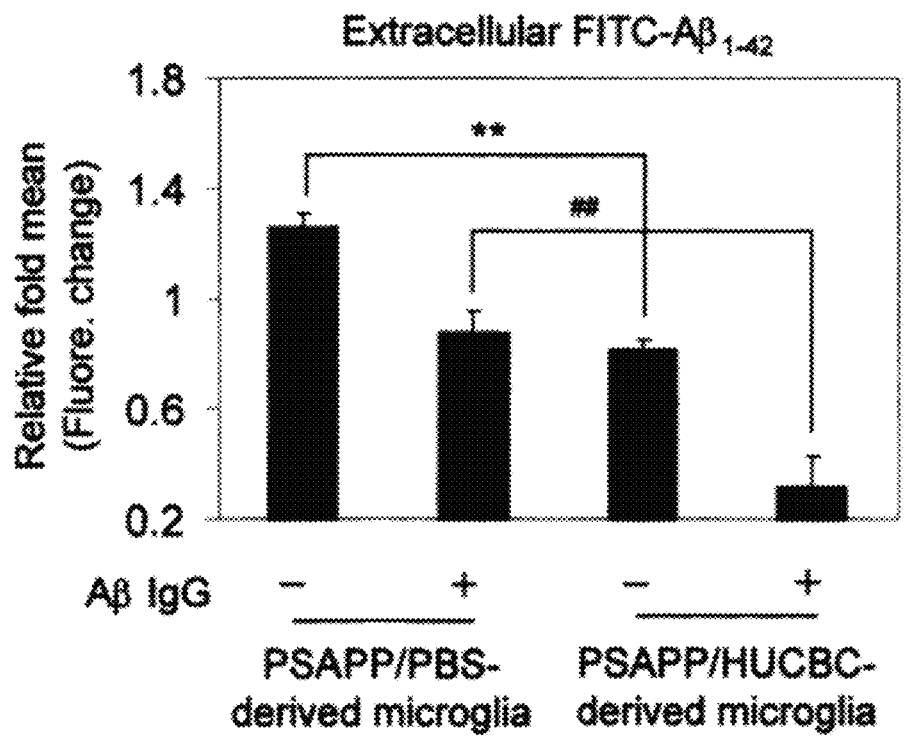
FIG. 19A is a graph showing HUCBC modulate microglial CD40 expression and promote Aβ microglial phagocytic activity. Microglial phagocytic assay for extracellular FITC-$A\beta_{1-42}$ in primary peripheral microglial cells from adult PSAPP/HUCBC or PSAPP/PBS mice. Signals were detected using a fluorometer and data represented as the relative fold of mean (±SD) fluorescence over control (primary microglial cells from adult PSAPP littermates) for each sample (n=4 for each condition presented).
Figure 19B:
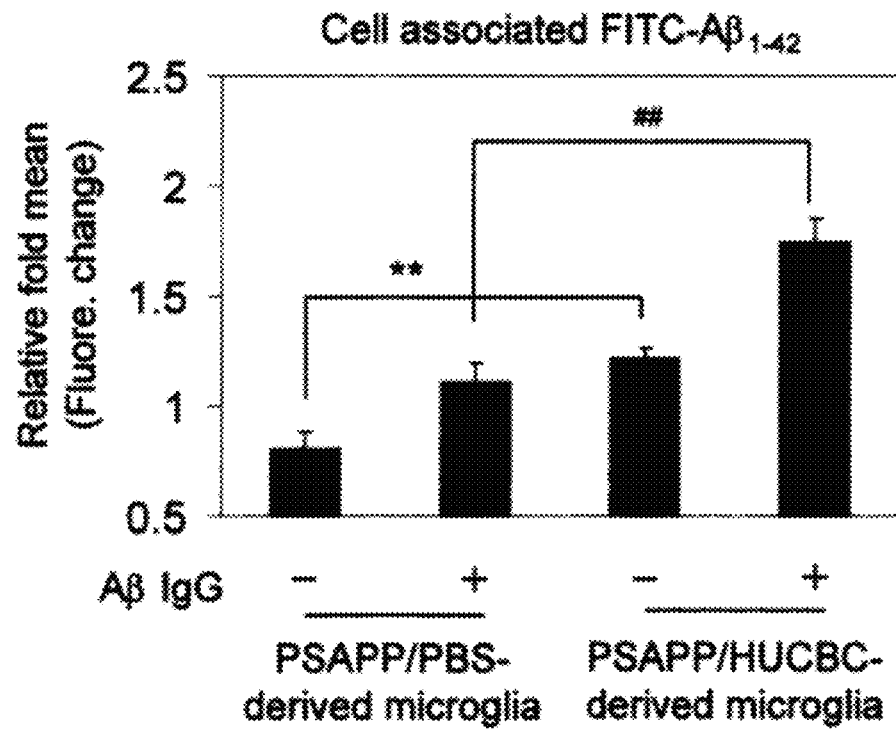
FIG. 19B is a graph showing HUCBC modulate microglial CD40 expression and promote Aβ microglial phagocytic activity. Microglial phagocytic assay for cell-associated FITC-$A\beta_{1-42}$ in primary peripheral microglial cells from adult PSAPP/HUCBC or PSAPP/PBS mice. Signals were detected using a fluorometer and data represented as the relative fold of mean (±SD) fluorescence over control (primary microglial cells from adult PSAPP littermates) for each sample (n=4 for each condition presented).
Figure 20A:
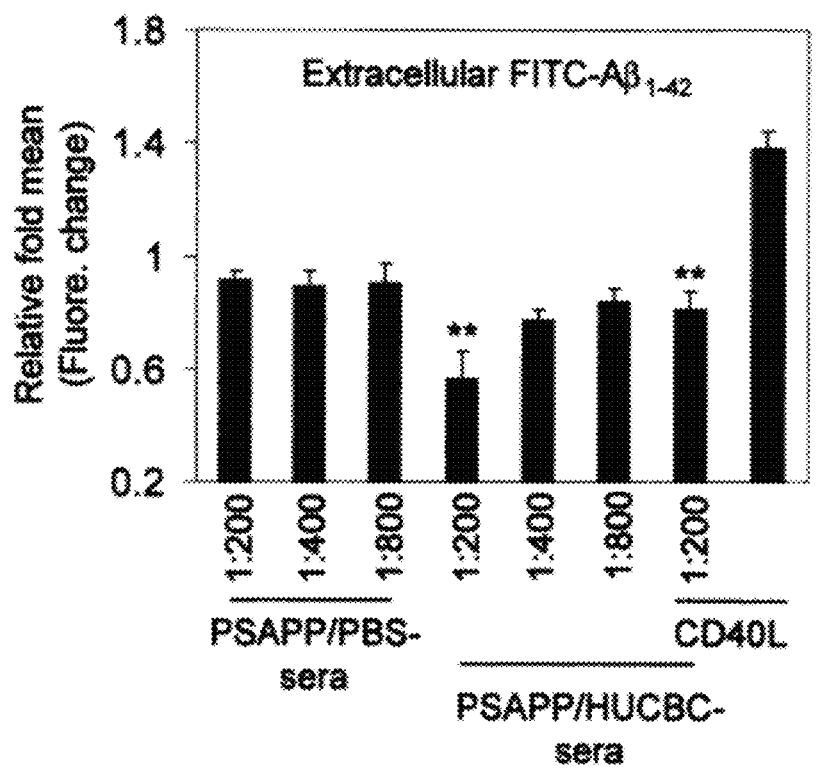
FIG. 20A is a graph showing HUCBC modulate microglial CD40 expression and promote Aβ microglial phagocytic activity. Microglial phagocytic assay for extracellular FITC-Aβ$_{1-42}$ in wild-type microglia. Signals were detected using a fluorometer and data represented as the relative fold of mean (±SD) fluorescence over control (primary microglial cells from adult PSAPP littermates) for each sample (n=4 for each condition presented).
Figure 20B:
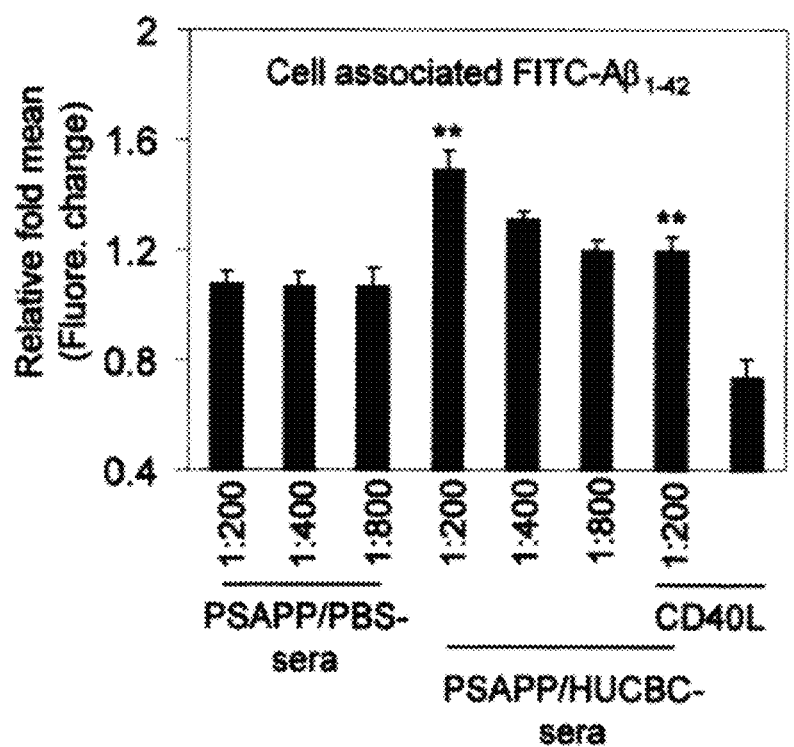
FIG. 20B is a graph showing HUCBC modulate microglial CD40 expression and promote Aβ microglial phagocytic activity. Microglial phagocytic assay for cell-associated FITC-Aβ$_{1-42}$ in wild-type microglia. Signals were detected using a fluorometer and data represented as the relative fold of mean (±SD) fluorescence over control (primary microglial cells from adult PSAPP littermates) for each sample (n=4 for each condition presented).

Stimulation of microglial CD40 signaling pathway results in impaired Aβ microglial phagocytic activity and promotion of microgial neurotoxic inflammatory responses. Thus, HUCBC were examined for the ability to enhance microglial phagocytosis of Aβ peptide. Primary cultures of adult microglia from HUCBC- and PBS-infused PSAPP mice were subjected to Aβ phagocytosis assay (Townsend, K., et al., CD40 signaling regulates innate and adaptive activation of microglia in response to amyloid beta-peptide. *Eur J Immunol*, 35:901-210, 2005; Lue, L., et al., Modeling Alzheimer's disease immune therapy mechanisms: interactions of human postmortem microglia with antibody-opsonized amyloid beta peptide. *J Neurosci Res*, 70:599-610, 2002) using 300 nM native or Aβ antibody-opsonized fluorescent-tagged $A\beta_{1-4}2$ (FITC-A). One-way ANOVA followed by post-hoc comparison of FITC-tagged $A\beta_{1-42}$ in cell supernatants or lysates showed a significant increase in Aβ uptake by microglia derived from HUCBC-infused PSAPP mice compared to PBS-infused PSAPP mice (P<0.001), as seen in FIGS. 19(A) and (B). Notably, the presence of Aβ IgG (2.5 μg/mL) significantly enhanced Aβ uptake by PSAPP/HUCBC mouse-derived microglial cells compared to PSAPP/PBS-derived microglial cells (##P<0.001). Given that sera from HUCBC-infused PSAPP mice suppressed IFN-γ-induced microglial CD40 expression, these effects were tested to determine the effect on microglial phagocytic activity. Primary microglial cells from neonatal mice were incubated with serum from individual PSAPP/HUCBC-versus PSAPP/PBS mice at 1:200, 1:400, and 1:800 dilutions in the presence of 300 nM FITC-$A\beta_{1-42}$. Sera diluted at 1:200 markedly enhanced microglial phagocytosis of $A\beta_{1-42}$ peptide, which was attenuated by the presence of recombinant mouse CD40L protein at 2 μg/mL, seen in FIGS. 20(A) and (B) (**P<0.001 with n=5 for each mouse group presented n=3 for CD40L alone condition).

Figure 21A:
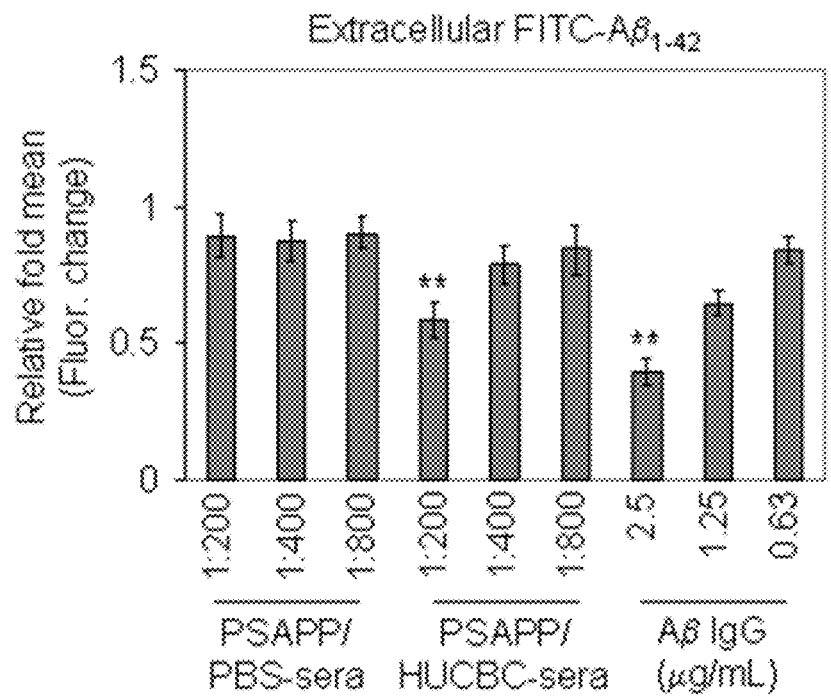
FIG. 21A is a graph showing HUCBC modulate microglial CD40 expression and promote Aβ microglial phagocytic activity. Microglial phagocytic assay for extracellular FITC-Aβ$_{1-42}$ in primary peripheral macrophages. Signals were detected using a fluorometer and data represented as the relative fold of mean (±SD) fluorescence over control (primary microglial cells from adult PSAPP littermates) for each sample (n=4 for each condition presented).
Figure 21B:
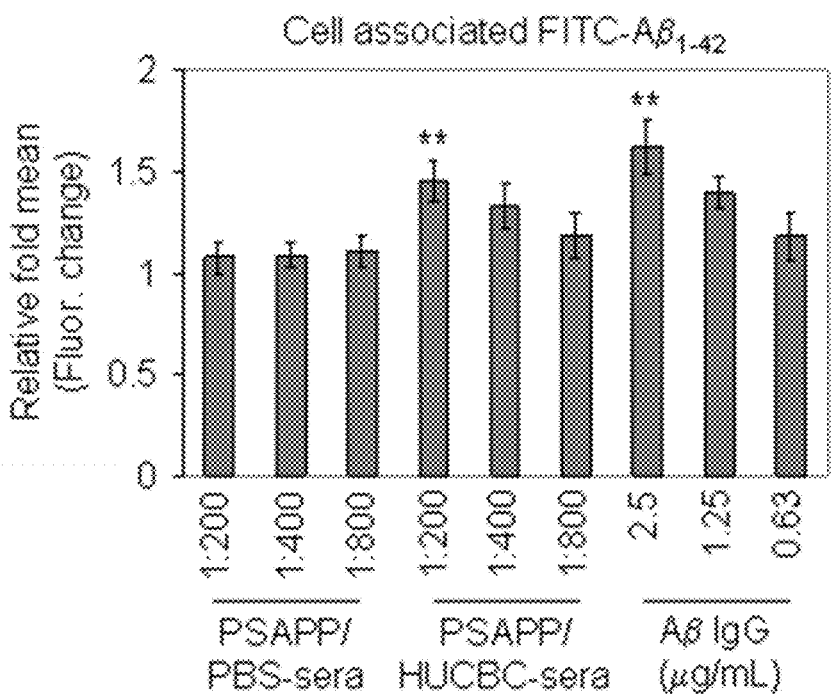
FIG. 21B is a graph showing HUCBC modulate microglial CD40 expression and promote Aβ microglial phagocytic activity. Microglial phagocytic assay for cell-associated FITC-Aβ$_{1-42}$ in primary peripheral macrophages. Signals were detected using a fluorometer and data represented as the relative fold of mean (±SD) fluorescence over control (primary microglial cells from adult PSAPP littermates) for each sample (n=4 for each condition presented).

The ability of HUCBC-derived sera was tested for the ability to increase peripheral macrophage phagocytic activity. Sera (50 μg/μL) derived from HUCBC-treated and PBS treated mice was incubated at 1:200, 1:400, and 1:800 dilutions with primary macrophages from wild-type mice in six-well tissue culture plates in the presence of 300 nM FITC-$A\beta_{1-42}$. Incubation with 1:200 sera significantly enhanced macrophage phagocytosis of $A\beta_{1-42}$ peptide, as seen in FIGS. 21(A) and (B) (**P<0.001 with n=4 for each treatment group presented). However, these effects were not observed in cultured HUCBC media (data not shown).

Increased CD40 signaling in AD, and reversal through CD40 or CD40L deficiency, or via application of CD40L antagonists results in diminished AD-like pathology. Infusing HUCBC mononuclear fraction into AD transgenic mice resulted in diminished Aβ/β-amyloid pathology with decreased CD40 signaling pathway activity and association with pro-inflammation. In addition to the ability to modulate the immune responses, HUCBC also produce a number of neurotrophic factors, including nerve growth factor, cytokine colony stimulating factor-1, thrombopoietin, and IL-11 (Vendrame, M., 2004; Suen, Y., et al., Decreased macrophage colony-stimulating factor mRNA expression from activated cord versus adult mononuclear cells: altered posttranscriptional stability. *Blood*, 84:4269-4277, 1994; McGowan, E., et al, Amyloid phenotype characterization of transgenic mice overexpressing both mutant amyloid precursor protein and mutant presenilin 1 transgenes. *Neurobiol Dis*, 6:231-244, 1999).

Administration of HUCBC mononuclear fraction into PSAPP and Tg2576 mice resulted in reduced levels of both soluble and insoluble $A\beta_{1-42}$, decreased Aβ deposits, and increased plasma Aβ levels. Thus, administration of HUCBC to PSAPP mice results in the production of neuroprotective substances, including nerve growth factor, cytokine colony stimulating factor-1, thrombopoietin, and IL-11, that could cross the blood-brain-barrier and reduce amyloidosis. Infusion of HUCBC mononuclear fraction into PSAPP and Tg2576 mice resulted in reduced levels of both soluble and insoluble $A\beta_{1,42}$, decreased Aβ deposits, and increased plasma Aβ levels. Thus administration of HUCBC to PSAPP mice results in the production of neuroprotective substances that cross the blood-brain-barrier and reduce amyloidosis.

The therapeutic benefits derived from HUCBC treatment may be owed to peripheral effects that signal CNS brain recovery mechanisms, affording CNS therapeutic benefit at a number of levels. On the same note, cerebral amyloid angiopathy has been demonstrated in 68% of AD patients.

Aβ is able to directly activate cultured vascular endothelial and smooth muscle cells by upregulating E-selectin/intercellular adhesion molecule-1 (ICAM-1) and CD40-CD40L in these cells. An abnormal accumulation of Aβ in the cerebrovasculature in CAA is associated with degeneration of these vessels (Cohen, D., et al, Amyloid-beta protein angiopathies masquerading as Alzheimer's disease, *Ann NY Acad Sci,* 826: 390-395, 1997), and $Aβ_{1-42}$ is highly associated with intracerebral hemorrhage (Cohen et al., 1997). IFN-γ, TNF-α, or LPS stimulation further up-regulates CD40 expression (Nguyen, V., et al., Post-transcriptional inhibition of CD40 gene expression in microglia by transforming growth factor-β, *Eur J Immunol,* 28:2537-2548, 1998; Aloisi, F., et al., Regulation of T-cell responses by CNS antigen-presenting cells: different roles for microglia and astrocytes. *Immunol Today,* 21: 141-147, 2000), explaining the higher levels of soluble CD40L levels of AD patients which further contributing to CD40-40L pathway and progression of CAA as well as brain inflammation. Tg2576, an established AD and CAA mouse model, infused with HUCBC showed decreased CAA levels by 86% as well as decreased Aβ/β-amyloid pathology. This was concomitant with demonstrated reduction of soluble CD40L in sera from HUCBC-infused PSAPP mice.

In adults, a balance between Th1 and Th2 cytokine networks has been proposed to be associated with a healthy status. An imbalance between Th1/Th2 cytokines among AD patients, clearly favoring the Th1 response in the AD, and the reversal, by CD40/CD40L deficiency or by application of CD40L antagonists, reduced AD-like pathology and rescued from cognitive impairment. HUCBC possesses an immunomodulatory role promoting a strong Th2 response (IL-4, IL-10, TGFβ) and reducing Th1 response (TNF-α, IL-12). These responses were specific to HUCBC since rodents infused with human adult mononuclear cells (HAMNC) did not yield any of these results and had similar results as the PBS treated or non treated groups (data not shown). This Th2 shift was demonstrated at both the CNS (brain homogenates) and the periphery (plasma, and primary culture splenocyte) in PSAPP HUCBC-infused mice over control group.

One of the main mediators for cytokine imbalance is the upregulation and activation of CD40 molecule. Microglia in PSAPP-infused mice have a decreased level of CD40 expression. As a result of, or in response to, decreased CD40 expression, the mice possess attenuated levels of microgliosis, astrocytosis, and a decreased co-localization of Aβ with astrocytes in the brain parenchyma was observed. This is in accordance with decreased Th1 cytokine levels from brain homogenates. Previous reports have shown that HUCBC do not enter the brain, and that the observed recovery following a brain injury is mediated through peripheral responses (Sanberg 2004). Thus the HUCBC's mode of action is attributable to modulation of CD40 signaling at the periphery. However, HUCBC-infused PSAPP mice-derived sera were able to reduce CD40 expression in cell culture microglia stimulated with IFN-γ, a phenomenon not seen in cell culture media derived from either HUCBC or human adult mononuclear plated cells. Furthermore, enhanced Aβ phagocytosis was observed following stimulation with the HUCBC-infused PSAPP mice-derived sera, suggesting CD40 responses are secondary to endogenous CD40 regulators that would normally be induced by the immune responses due to HUCBC infusion.

Examples

Transgenic PSAPP (APPswe, PSEN1dE9; Jackson Laboratory, Bar Harbor, Me.) and Tg2576 (Taconic, Inc., Hudson, N.Y.) mice were intravenously (i.v.) treated starting at 7 months of age (visible Aβ histological deposit formation of age. These mice were treated with HUCBC (100,000 cells/mouse, 98% mononuclear cells; Saneron CCEL Therapeutics, Inc., Tampa, Fla.) or PBS biweekly for the first two months and monthly for the remaining four months (n=10/group, 5♂/5♀). Blood was collected by submandibular bleeding at 0, 2, 4 and 6 months to monitor plasma cytokine, sCD40L and Aβ changes throughout the study. The mouse brains were analyzed for Aβ deposits and gliosis at 13 months of age, when the mice typically manifest well established AD-like pathology. PSAPP mice deficient in CD40 and controls were treated at 8 weeks of age, when Aβ proteins reach detectable levels. Blood was collected by submandibular bleeding at two months following treatment.

Mice were anesthetized with isofluorane and transcardially perfused with ice-cold physiological saline containing heparin (10 U/mL). Brains were rapidly isolated and quartered using a mouse brain slicer (Muromachi Klkai, Tokyo, Japan). The first and second anterior quarters were homogenized for Western blot analysis, and the third and fourth posterior quarters were used for microtome or cryostat sectioning. Brains were then fixed in 4% paraformaldehyde in PBS at 4° C. overnight and routinely processed in paraffin in a core facility at the Department of Pathology (USF College of Medicine). Five 5 μm thick coronal sections from each brain were cut with a 150 μm interval-for cingulated cortex (CC) bregma −0.10 mm to −0.82 mm; for entorhinal cortex (EC) and hippocampus (H), bregina −2.92 mm to −3.64 mm. Sections were routinely deparaffinized and hydrated in a graded series of ethanol before preblocking for 30 min at ambient temperature with serum-free protein block (Dako Cytomation, Carpinteria, Calif.). Aβ immunohistochemical staining was performed using anti-human amyloid-β antibody (4G8) in conjunction with the VectaStain Elite ABC kit (Vector Laboratories, Burlinganie, Calif.) coupled with diaminobenzidine substrate. 4G8-positive Aβ deposits were examined under bright field using an Olympus (Tokyo, Japan) BX-51 microscope. Congo red staining was done according to standard practice using 10% (w/v) filtered Congo red dye cleared with alkaline alcohol. These sections were rinsed three times for 5 min each in 70% ethanol, hydrated for 5 min in PBS, and mounted in Vectashield fluorescence mounting media (Vector Laboratories). Congo red-positive β-amyloid plaques were visualized under bright field using an Olympus BX-51 microscope. Aβ burden was determined by quantitative image analysis using threshold optical density and discriminated staining from background. Manual editing of each field was used to eliminate artifacts. Data are reported as percentage of immunolabeled area captured (positive pixels divided by total pixels captured). Quantitative image analysis was performed by a single examiner (TM) blinded to sample identifies.

Immunofluorescence and Co-Localization Analysis

Aβ/microglia co-localization was performed using rat anti-mouse CD40 (1:1000) and rabbit anti-pan Aβ (1:100; Biosource International, Inc., Camarillo, Calif.) overnight followed by goat anti-rat IgG FITC (1:50; PharMingen, Los Angeles, Calif.) and donkey anti-rabbit Alexa Fluor555 (1:500; Invitrogen, Carlsbad, Calif.) for 45 mm for Aβ/microglia; Aβ/astrocyte colocalization was performed using a biotinylated human amyloid-β monoclonal antibody (4G8; 1:100, Signet Laboratories, Dedham, Mass.) and GFAP polyclonal antibody (1:500, DAKO, Carpinteria, Calif.). Normal rabbit or normal mouse serum (isotype control) or phosphate buffered saline (PBS, 0.1 M, pH 7.4) was used instead of primary antibody or ABC reagent as a negative control. Quantitative image analysis was done based on a previous method with modifications. Images were acquired as digitized tagged-image format files to retain maximum resolution using an Olympus BX60 microscope with an attached digital camera system (DP-70, Olympus, Tokyo, Japan), and digital images were routed into a Windows PC for quantitative analyses using SimplePCI software (Compix, Inc. Imaging Systems, Cranberry Township, Pa.). The cingulate cortex region was captured from the image of the cortex adjacent to the sagital fissure, and the entothinal region was captured from the image of the cortex ventral to the entorhinal fissure. In images from cingulate and entorhinal regions, the cortical edge was not included to allow capture of the full anatomic region of interest. The hippocampus region was captured from between a portion of the CA1 subfield of the pyramidal cell layer and the lacunosum molecular layer. The anatomical locations and boundaries of the regions analyzed were based on those defined (Mori, T., et al., Arundic acid ameliorates cerebral amyloidosis and gliosis in Alzheimer transgenic mice. *J Pharmacol Exp Ther*, 318:571-578). Images of five 5 µm sections through each anatomic region of interest were captured, and a threshold optical density was obtained that discriminated staining from background. Each anatomic region of interest was manually edited to eliminate artifacts. For Aβ and GFAP (astrocytosis) burden analyses, data are represented as percentage of immunolabeled area captured (positive pixels) relative to the full area captured (total pixels).

Flow Cytometric and Western Blot Analyses for CD40 Expression

Primary cultured microglial cells were plated in 6-well tissue culture plates at $5 \times 10^5$ cells/well and incubated with IFN-γ (100 ng/mL) in the presence or absence of sera derived HUCBC- or PBS-infused PSAPP mice. Twelve hours after incubation, microglial cells were washed with flow buffer, consisting of PBS containing 0.1% (w/v) sodium azide and 2% (v/v) FCS, and resuspended in 250 µl of ice-cold flow buffer for fluorescence activated cell sorting (FACS) analysis, as described previously (Tan, J., et al., Introduction of CD40 on human endothelial cells by Alzheimer's beta-amyloid peptides. *Brain Res Bull*, 50:142-148, 1999). Cells were washed, resuspended in flow buffer, and analyzed by a FACScan instrument (Becton Dickinson, Franklin Lakes, N.J.). A minimum of 10,000 cells were accepted for FACS analysis. Cells were gated based on morphological characteristics such that apoptotic and necrotic cells were not accepted for FACS analysis using CellQuest software (Becton Dickinson). Percentages of positive cells (CD40-expressing) were calculated as follows: for each treatment, the mean fluorescence value for the isotype-matched control antibody was subtracted from the mean fluorescence value for the CD4O-specific antibody.

For Western blot of brain CD40 expression, mouse brain homogenates were prepared from HUCBC-I and PBS-infused PSAPP mice as previously described (Tan, J., et al., Role of cD40 ligand in transgenic Alzheimer's mice. *Nat Neurosci*, 5:1288-1293, 2002). 100 µg of total protein of each sample was separated by SDS-PAGE and transferred electrophoretically to immunoblotting PVDF membranes. The membranes were hybridized with rabbit anti-CD40 antibody (1:1,500 dilution; StressGen, Victoria, Canada) for 2 hrs and immunoblotted using anti-rabbit HRP-conjugated IgG secondary antibody as a tracer and incubated in luminol reagent. To demonstrate equal loading the membranes were stripped with β-mercaptoethanol stripping solution and re-probed with anti-actin mouse monoclonal antibody. Densitometric analysis was done as previously described using a FluorS Multiimager with Quantity One software (BioRad, Hercules, Calif.) (Tan, J., et al., 2002).

Aβ and Cytokine ELISA

Mouse brains were isolated under sterile conditions on ice and placed in ice cold lysis buffer as previously described (Tan, J., et al., 2002). Brains were then sonicated on ice for approximately 3 minutes allowed to stand for 15 minutes at 4° C., and centrifuged at 15,000 rpm for 15 minutes. This fraction represented the detergent-soluble fraction. $A\beta_{1-40, 42}$ species were further subjected to acid extraction of brain homogenates in 5 M guanidine buffer, followed by a 1:5 dilution in lysis buffer. Soluble $A\beta_{1-40, 42}$ were directly detected in plasma and brain homogenates prepared with lysis buffer described above at a 1:5 or 1:10 dilution in dilution buffer (PBS+1% BSA+PMSF), respectively. $A\beta_{1-40, 42}$ was quantified in these samples using the $A\beta_{1-40, 42}$ ELISA kits (IBL-America, Minneapolis, Minn.) in accordance with the manufacturer's instructions, except that standards included 0.5 M guanidine buffer in some cases. $A\beta_{1-40, 42}$ were represented as pg/mL of plasma and pg/mg of total protein (mean±SD).

Cell suspensions of splenocytes from individual mice were prepared as previously described (Town, T., et al., Reduced Th1 and enhanced Th2 immunity after immunization with Alzheimer's beta-amyloid (1-41). *J Neuroimmunol*, 132:49-59, 2002) and passed in 0.5 mL aliquots into 24-well plates at $3 \times 10^6$/mL. These cells were treated for 48 hrs with ConA (5 µg/mL). Supernatants were then collected and assayed by IL-10, TNF-α, and IL-12(p70) cytokine ELISA kits in strict accordance with the manufacturer's instruction (R&D Systems). The Bio-Rad protein assay (Bio-Rad Laboratories, Hercules, Calif.) was performed to measure total cellular protein from each of the cell groups under consideration just prior to quantification of cytokine release by ELISA, and cytokine secretion is expressed in pg/mg total cellular protein (mean±SD). To verify whether stimulation of splenocytes produced any between-groups differences on cell death that might account for altered cytokine profiles, LDH release assay was carried out as described (Town, T., et al., Reduced Th1 and enhanced Th2 immunity after immunization with Alzheimer's beta-amyloid(1-42). *J Neuroimmunol*, 132:49-59, 2002) and LDH was not detected in any of the wells studied. ELISA for IgM and IgG were performed as previously described (Nikolic, W., et al., Transcutaneous beta-amyloid deposits without T-cell infiltration and microhemmorhage. *Proc Nat Acad Sci USA*, 104:2507-2512, 2007) and optical densities determined by microplate reader at 450 nm. The ratio of IgM to IgG was calculated by optical density. Brain tissue-derived (supernatants from the brain homogenates) and serum-derived (plasma) samples were analyzed for IL-4, IL-10, IL-2, IFN-γ, TNF-α, IL-1β, IL-12 (p70), and TGF-β cytokines by Bioplex assays (Bio-Rad Laboratories, Hercules, Calif., USA), according to the manufacturers protocol.

Microglial Phagocytosis Assay

Primary murine microglia cultures were seeded at $1 \times 10^5$ cells/well (n=6 for each condition) in RPMI-1640, as described previously (Townsend, K., et al., CD40 signaling regulates innate and adaptive activation of microglia in response to amyloid beta-peptide. *Eur J Immunol*, 35:901-910, 2005). These cells were treated for 60 min with "aged" $A\beta_{1-42}$ conjugated with FITC (Biosource International) (Townsend, K., 2005). In the presence of FITC-$A\beta_{1-42}$, microglia were co-treated with sera (1/200, 1/400, 1/800 dilution) derived from HUCBC- or PBS-infused PSAPP mice in the presence or absence of CD40L protein (2

μg/mL). Microglia were then rinsed 3 times in Aβ-free complete medium, and the media were exchanged with fresh Aβ-free complete medium for 10 min both to allow for removal of non-incorporated Aβ and to promote concentration of the Aβ into phagosomes. Extracellular and cell associated FITC-Aβ were quantified using a MSF (Spectra-Max®, Molecular Devices) with an emission wavelength of 538 nm and an excitation wavelength of 485 nm. A standard curve from 0 nM to 500 nM of FITC-Aβ was run for each plate. Total cellular proteins were quantified using the Bio-Rad protein assay and mean fluorescence values determined at 37° C. by fluorometic analysis. Relative fold change values were calculated as: (mean fluorescence value for each sample at 37° C./mean fluorescence value over control). LDH assay was performed on the supernatant to determine the extent to which cell death might have influenced the phagocytic activity in the various treatment groups. Data showed that there was no significant cell death occurring over the 3 hrs time-frame in any of the treatment groups ($p>0.05$).

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosure of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall therebetween.

What is claimed is:

1. A method of treating amyloid beta associated disease, comprising the step of:
    administering a biological composition of human umbilical cord blood cell-derived plasma to a patient suffering from an amyloid beta associated disease.
2. The method of claim 1, wherein the amyloid beta associated disease is at least one disease selected from the group consisting of Alzheimer's disease, cerebral amyloid angiopathy, Huntington's disease, and type II diabetes.
3. The method of claim 1, wherein the human umbilical cord blood cell-derived plasma is formed using a substantially purified mononuclear cell fraction of human umbilical cord blood cells.
4. The method of claim 1, wherein the biological composition is peripherally administered.
5. The method of claim 1, wherein the biological composition is administered in multiple doses.
6. The method of claim 1, wherein the biological composition modulates at least one peptide selected from the group consisting of CD40 and CD40L.
7. The method of claim 1, wherein the umbilical cord blood cell-derived plasma is administered at a dilution selected from the group consisting of 1:200, 1:400, and 1:800.
8. The method of claim 1, wherein the umbilical cord blood cell-derived plasma is obtained through the steps:
    administering an effective amount of human umbilical cord blood cells to an organism;
    allowing the organism to mount a response to the human umbilical cord blood cells; and
    collecting blood plasma from the organism after the mounted response to the human umbilical cord blood cells.
9. A method of treating an amyloid beta associated disease comprising
    modulating an inflammatory response in a patient suffering from an amyloid beta associated disease; and
    modulating the levels of at least one protein selected from the group consisting of detergent soluble A-beta peptide, detergent insoluble A-beta peptide, CD40, and CD40L, by administering a biological composition of human umbilical cord blood cell-derived plasma to the patient.
10. The method of claim 9, wherein the amyloid beta associated disease is at least one disease selected from the group consisting of Alzheimer's disease, cerebral amyloid antigopathy, Huntington's disease, and type II diabetes.
11. The method of claim 9, wherein the human umbilical cord blood cell-derived plasma is formed using a substantially purified mononuclear cell fraction of human umbilical cord blood cells.
12. The method of claim 9, wherein the biological composition is peripherally administered.
13. The method of claim 9, wherein the biological composition is administered in multiple doses.
14. The method of claim 9, wherein the inflammatory response is modulated through modulating the phagocytic activity of at least one immune cell line selected from the group consisting of microglia, macrophages, and astrocytes.
15. The method of claim 9, wherein the umbilical cord blood cell-derived plasma is administered at a dilution selected from the group consisting of 1:200, 1:400, and 1:800.
16. The method of claim 9, wherein the inflammatory response is modulated through modulating cytokine levels.
17. The method of claim 9, wherein the umbilical cord blood cell-derived plasma is obtained through the steps:
    administering an effective amount of human umbilical cord blood cells to an organism;
    allowing the organism to mount a response to the human umbilical cord blood cells; and
    collecting blood plasma from the organism after the mounted response to the human umbilical cord blood cells.

* * * * *